US007522756B2

(12) United States Patent
Bueno et al.

(10) Patent No.: US 7,522,756 B2
(45) Date of Patent: Apr. 21, 2009

(54) METHOD, SYSTEM AND APPARATUS FOR PROCESSING RADIOGRAPHIC IMAGES OF SCANNED OBJECTS

(75) Inventors: Clifford Bueno, Clifton Park, NY (US); Elizabeth Lokenberg Dixon, Delanson, NY (US); Walter Vincent Dixon, Delanson, NY (US); Forrest Frank Hopkins, Cohoes, NY (US); Michael Robert Hopple, Scotia, NY (US); Brian Walter Lasiuk, Waukesha, WI (US); Ronald Cecil McFarland, Cincinnati, OH (US); August David Matula, Fredericksburg, VA (US); Robert James Mitchell, Jr., Waterford, NY (US); Kevin Layne Moermond, Cincinnati, OH (US); Gregory Alan Mohr, West Chester, OH (US)

(73) Assignee: General Electric Company, Niskayuna, NY (US)

( * ) Notice: Subject to any disclaimer, the term of this patent is extended or adjusted under 35 U.S.C. 154(b) by 250 days.

(21) Appl. No.: 11/684,176

(22) Filed: Mar. 9, 2007

(65) Prior Publication Data

US 2008/0166033 A1 Jul. 10, 2008

Related U.S. Application Data

(62) Division of application No. 10/456,280, filed on Jun. 5, 2003, now Pat. No. 7,215,801.

(51) Int. Cl.
*G06K 9/00* (2006.01)
(52) U.S. Cl. .................. 382/132; 382/141
(58) Field of Classification Search ................. 382/132, 382/141, 152, 307; 378/57, 58, 62; 715/965; 713/1, 100; 702/85
See application file for complete search history.

(56) References Cited

U.S. PATENT DOCUMENTS

| 5,422,805 A | 6/1995 | McIntyre et al. ............ 364/757 |
| 5,519,441 A | 5/1996 | Gusmano et al. ............ 348/207 |
| 5,594,854 A | 1/1997 | Baldwin et al. ............. 395/141 |
| 5,684,728 A | 11/1997 | Okayama et al. .......... 364/736.5 |
| 5,874,909 A | 2/1999 | Soenen et al. ............... 341/141 |
| 6,314,443 B1 | 11/2001 | Seal ........................... 708/552 |

(Continued)

*Primary Examiner*—Andrew W Johns
(74) *Attorney, Agent, or Firm*—Penny A. Clarke (57) ABSTRACT

A method, system and apparatus for processing a radiographic image of a scanned object is disclosed. A pixel offset correction is performed in integer format on the radiographic image using saturation arithmetic to produce an image in integer format with any negative corrected values clipped to a value of zero. The resulting pixels are converted to floating point format and the converted pixels are multiplied by a gain factor. Optionally the resulting pixels are recursively averaged with previous results. The resulting pixels are converted to integer format and the converted pixel values are clamped to a maximum value using saturation arithmetic. Non-functional pixel correction is performed in integer format and the resulting pixel values are clamped to a maximum value using saturation arithmetic. An optional processing path replaces the recursive average by a linear average. The resulting pixel values are optionally filtered to enhance features of interest. The resulting pixel value is mapped in integer format to a palette index to establish an output pixel intensity having one of many intensity levels. The optional processing is controlled through the hardware interface of a real-time image controller as images are acquired.

15 Claims, 9 Drawing Sheets

U.S. PATENT DOCUMENTS 6,504,895 B1    1/2003   Dixon et al. .................. 378/19
7,394,925 B2 *  7/2008   Hayashida .................. 382/132
2005/0008120 A1 * 1/2005  Ellenbogen .................. 378/57

* cited by examiner

METHOD, SYSTEM AND APPARATUS FOR PROCESSING RADIOGRAPHIC IMAGES OF SCANNED OBJECTS

This application is a division of application Ser. No. 10/456,280, filed Jun. 5, 2003, now U.S. Pat. No. 7,215,801.

BACKGROUND OF THE INVENTION

The present invention relates generally to a method, system, and apparatus for processing radiographic images of scanned objects, and particularly to a method, system, and apparatus for processing radiographic images in real-time using a commercial off the shelf processor, a graphical user interface for setup and control, and a programmable commercial off the shelf controller box.

Radiography is the technique of producing an image of any opaque specimen by the penetration of radiation, such as gamma rays, x-rays, neutrons, or charged particles. When a beam of radiation is transmitted through any object, the radiation is differentially absorbed depending upon variations in object thickness, density, and chemical composition. The energy emergent from the object forms a radiographic image, which may then be realized on an image detection medium, such as a radiation sensitive detector having an array of elements that generate a signal output depending on the level of radiation absorbed, the detector signal output being converted into a voltage proportional to the level of radiation absorbed by the detector elements. Radiography is a non-destructive technique for examining the internal structure of an object, and is conventionally used in medical and industrial applications. Radiography is used to detect medical conditions such as tuberculosis and bone fractures, as well as manufacturing imperfections in materials such as cracks, voids, and porosity.

In industrial applications, digital radiographic systems tend to be designed for inspection of specific components and require highly trained operators to setup and operate, limitations that make them expensive to purchase and manage. Accordingly, there is a need in the art for advances in industrial radiographic systems having a lower cost and improved ease-of-use.

SUMMARY OF THE INVENTION

In one embodiment, a method of processing a radiographic image of a scanned object is disclosed. A pixel offset correction is performed in integer format on the radiographic image using saturation arithmetic to produce an image in integer format with any negative corrected values clipped to a value of zero. The resulting pixels are converted to floating point format and multiplied by a positive floating point gain factor. The resulting pixels are converted to integer format such that the resultant converted pixel values are clamped to a maximum value using saturation arithmetic. Non-functional pixel correction is performed in integer format and the resulting pixel values are clamped to a maximum value using saturation arithmetic. The range of the resulting pixel value is mapped to one compatible with an output display device. Specifically, the input resulting pixel value is converted to a palette index to establish an output pixel intensity for display on a computer monitor. Because the monitor has limited bit depth, more than one distinct pixel value may produce the same palette index.

In another embodiment, a computer program article for carrying out the method described above is disclosed. In addition to including instructions for execution by a commercial "off-the-shelf" processor for executing the disclosed method above, the computer program article also includes instructions for filtering the mapped radiographic image to enhance feature recognition within the thickness range of the scanned object, and for displaying the filtered radiographic image in real-time at a frame rate of equal to or greater than an equivalent rate of 30 million pixels per second.

In a further embodiment, a radiographic inspection system includes a computer adapted to be in signal communication with an imaging system, which is adapted to acquire and output radiographic image data of a scanned object, and a real-time image controller in signal communication with the computer. The computer includes a processor to execute operations according to a set of instructions provided by installed application software, memory to store application software and to store the image data, and an input device and a display device operable as a graphical user interface to configure and operate the inspection system. The real-time image controller includes a set of image control buttons and a set of image control dials, and an application programming interface to map the functions of the control buttons and dials to the application software.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the present invention provides a non-destructive radiographic inspection system that dynamically processes radiographic images in real-time using a plurality of one or more commercial off the shelf (COTS) processors having native saturation arithmetic capability, a graphical user interface for configuring and operating the radiographic inspection system, and a real-time image controller for controlling individual acquisition sequences. Saturation arithmetic refers to a known processor characteristic where calculations are clipped to a range. The specific nature of the clipping depends on whether one performs signed or unsigned arithmetic. Signed saturated subtraction clips the result to the largest negative value that the bit-depth can support. Unsigned saturated subtraction clips the result to zero. Saturated addition clips the result to the largest positive value that the bit depth can support. For a given bit depth numerical range depends on whether a quantity is treated as a signed or unsigned value. While the embodiment described herein depicts x-rays as an exemplary type of radiation for radiographic imaging, it will be appreciated that the disclosed invention is also applicable to other radiation types, such as gamma rays, high-frequency sound waves, magnetic fields, neutrons, or charged particles for example.

Figure 1:
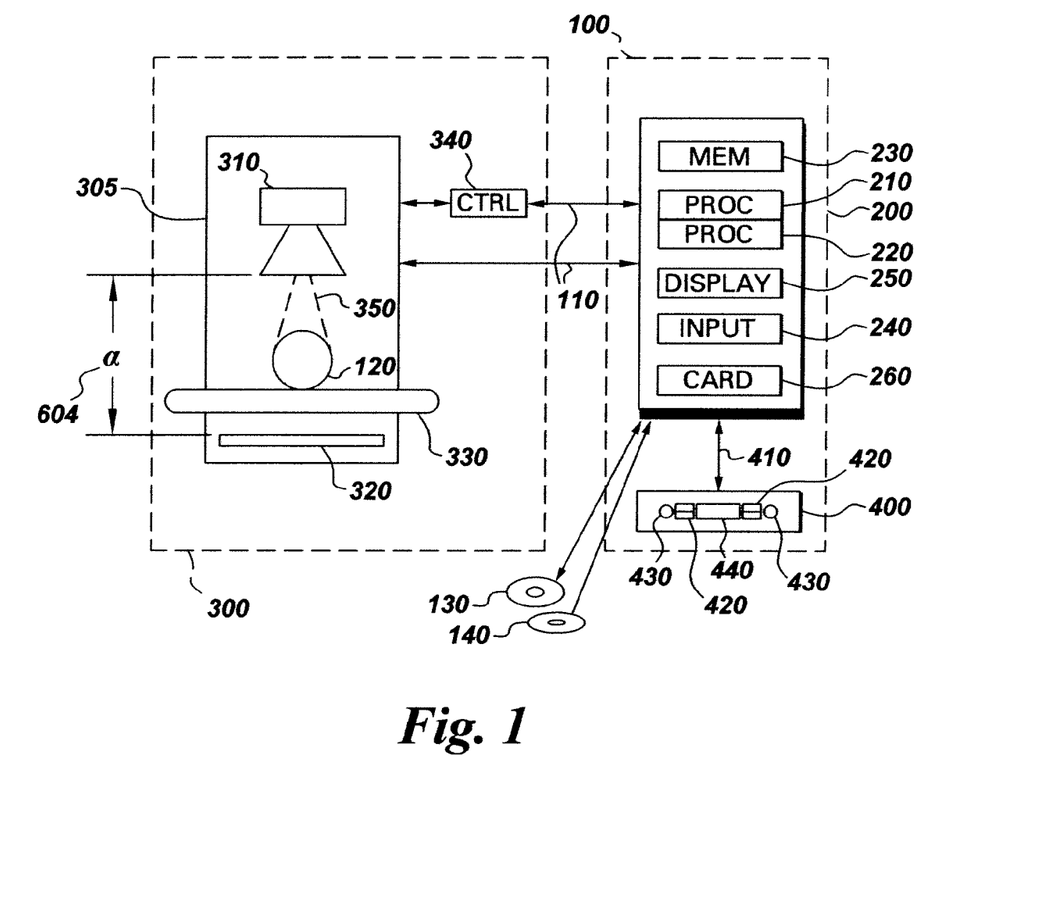
FIG. 1 depicts an exemplary system for implementing an embodiment of the invention.

FIG. 1 is an exemplary embodiment of a radiographic inspection system 100 that includes a computer 200 adapted to be in signal communication with an imaging system 300 via a communication bus 110, and a real-time image controller 400 adapted to be in signal communication with computer 200 via a communication bus 410. Imaging system 300 is adapted to acquire and output radiographic image data of a scanned object 120 via an imaging device 305, which includes an x-ray source 310, an image detector 320, and an object manipulator 330. Imaging system 300 also includes an imaging system controller 340 that receives control commands from computer 200 and sends control signals to the various components of imaging device 305. Manipulator 330 may be a conveyor belt, a reversible table, or any other suitable device for manipulating object 120 into and out of the x-ray beam 350.

Computer 200 includes one or more processors 210, 220 to execute operations according to a set of instructions provided by installed application software, discussed further below, a detector interface card 260, also discussed further below, at least one memory 230 to store the application software and to store the image data received from image detector 320, an input device 240, and a display device 250. Memory 230 refers to any type and number of memory chips, magnetic storage disks, optical storage disks, mass storage devices, or any other storage device suitable for retaining information. Input device 240 may be a keyboard, a mouse, a pointing device, a touch sensitive screen device, a tablet, a read/write drive for a magnetic disk, a read/write drive for an optical disk, a read/write drive for any other input medium, an input port for a communication link (electrical or optical), a wireless receiver, or any combination thereof, for example. Display device 250 may be a CRT (cathode ray tube) screen or any other suitable display device for displaying text, graphics, and a graphical user interface, for example. Input device 240 and display device 250 operate in combination to provide a graphical user interface, discussed in more detail below, that enables a user or operator to configure and operate inspection system 100. Detector interface card 260 provides low level control over the image detector, buffers data read out from the image detector, and optionally reorders image pixels to convert from read-out order to display order.

Real-time image controller (RTIC) 400 includes a set of image control buttons 420, a set of image control dials 430, a display 440, and an embedded application programming interface that maps the functions of control buttons and dials 420, 430 to the application software at computer 200. RTIC 400 is discussed further below with reference to FIG. 10.

Figure 2:
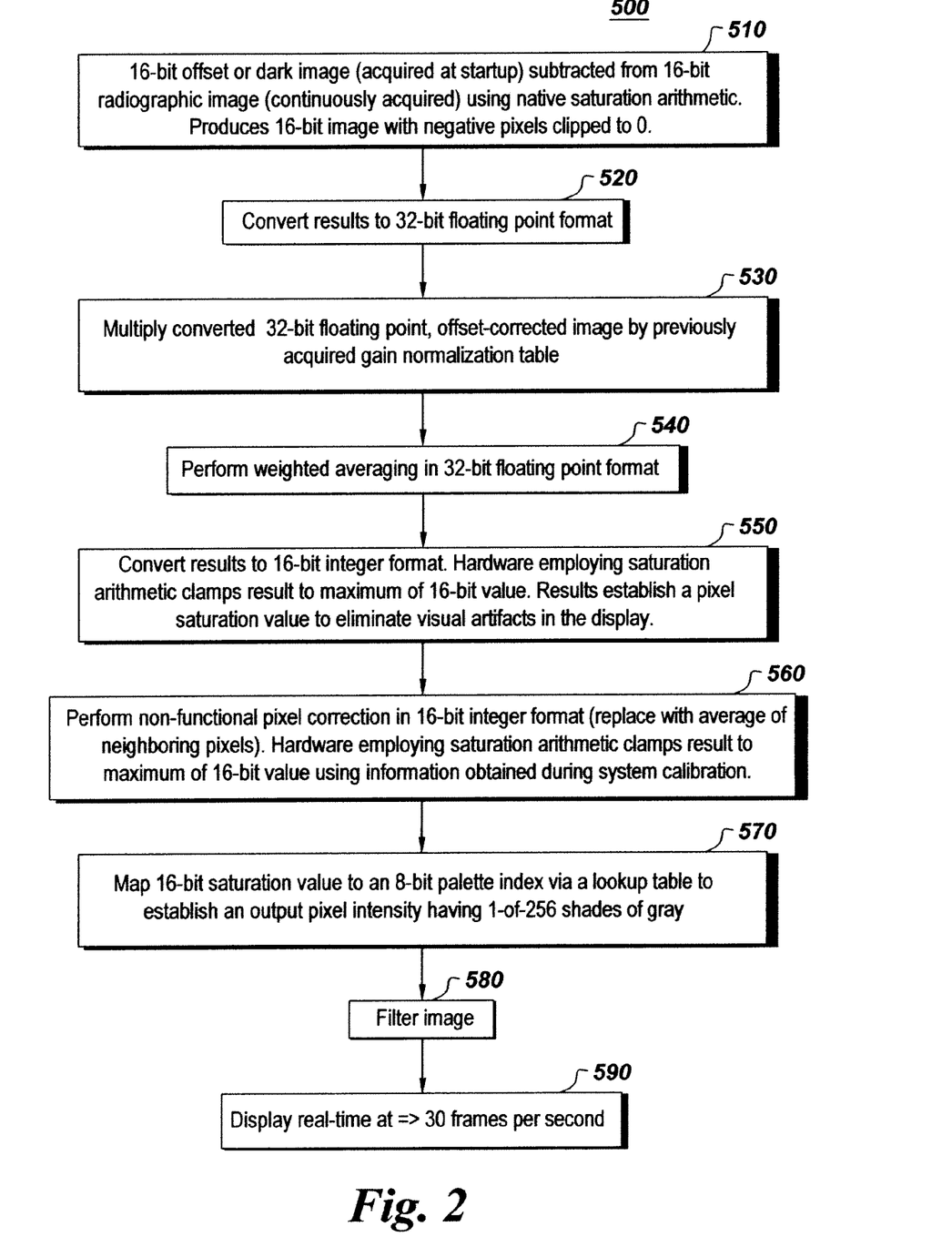
FIG. 2 depicts an exemplary process flow diagram in accordance with an embodiment of the invention.

In exemplary embodiments, processors 210, 220 are a 1.7 GHz or faster Intel Pentium 4 processor and a 2.4 GHZ or faster Intel Xeon processor, respectively, that are programmed to process radiographic image data of scanned object 120 according to the process 500 depicted in FIG. 2. Referring now to FIG. 2, process 500 begins at block 510 by performing in 16-bit integer format a pixel offset correction on the 16-bit radiographic image using native saturation arithmetic to produce an image in 16-bit integer format having negative value pixels clipped to a value of zero. In an embodiment, the pixel offset correction involves subtracting dark image (alternatively offset image) pixel values from the radiographic image pixel values, where dark image refers to an image data set acquired in the absence of x-rays and stored at memory 230. As used herein, reference to an operation on a pixel means an operation on the intensity value of the pixel. When system 100 is operating in real-time mode, the 16-bit radiographic images are continuously acquired at imaging device 305, processed by one or more processors 210, 220, and displayed at display 250 at a frame rate equivalent to 30 million pixels per second.

At blocks 520-530, the processor(s) 210 adds the results of block 510 to a 32-bit integer accumulation of zero or more previously offset-corrected images to provide an accumulated offset corrected image in 32-bit integer format, converts the sum to a 32-bit floating point number, and multiplies the converted pixels by a 32-bit positive floating point gain factor acquired from a normalization table at memory 230.

At block 540, weighted averaging (recursive averaging) is performed using 32-bit floating point arithmetic on the gain-multiplied pixels. In an embodiment, weighted averaging involves applying an exponential weighting function to the intensity of the pixels in successive frames, the older the frame the smaller the weight, thereby imparting greater weight to the intensity of the pixels in the most recent frames, however, other weighting functions, or no weighting function, may also be employed. In an embodiment, an average image value may be calculated by dividing, or multiplying by a reciprocal value, the resulting pixel value, which is a sum of accumulated pixel values, by the number of accumulated images.

At block 550, the results of block 540 are divided by the number of accumulated images and converted to 16-bit integers using saturation arithmetic. Native saturation arithmetic also clamps the 16-bit integers to the maximum value available in 16-bit integer format and to a minimum value of zero, thereby establishing a pixel saturation value that eliminates visual artifacts in the display. The clamped pixel values are clamped to an appropriate 16 bit range and not allowed to wrap. The nature of the operation and the size of the operands determine the appropriate range. For example, using 16-bit operands and unsigned saturated subtraction, the result is clipped to 0. Using 16-bit operands and signed subtraction, the result is clipped to $-2^{15}$.

At block 560, processor(s) 210 performs in 16-bit integer format a non-functional pixel correction by replacing a non-functional pixel with the average pixel intensity value of the neighboring pixels. Other non-functional pixel correction routines may be employed in place of the "average-of-the-neighbors" routine. In an embodiment, a non-functioning pixel is identified during system calibration. The corrected image is then processed using native saturation arithmetic to clamp the pixel values to the maximum value available in 16-bit integer format. The user may in real-time adjust the number of frames that the linear averaging is applied to, thereby obtaining a visually optimal display.

At block 570, the resulting 16-bit corrected pixel value is mapped to display resolution in integer format to an 8-bit palette index via a lookup table at memory 230 to establish an output pixel intensity having one-of-many, such as 1-of-256 for example, intensity levels, which in an embodiment are displayed as shades of gray. In an embodiment, a single lookup table incorporating both contrast management and gamma correction is used to map the integer resulting pixel to an 8 bit gray scale image suitable for display on a standard monitor. Contrast management can include window/level, histogram equalization, or any other standard image processing technique. Combining the contrast management with the gamma correction avoids the posterization effect produced by using two separate lookup tables. Posterization is a known phenomena in which tiny rectangular regions due to truncation are visible in an image. At blocks 580, 590, the mapped image is filtered to enhance feature recognition within the thickness range of scanned object 120 and displayed at a real-time frame rate of equal to or greater than an equivalent of 30 million pixels per second. In an embodiment, the filter is a standard image processing filter including but not limited to a high-pass filter, a low-pass filter, a sharpening filter, an edge enhancement filter, or a filter with a custom kernel, used singly or cascaded. Multiple filters may be employed with each tuned to identify a specific type of defect. For example, a low-pass filter may be included to enhance detection of inclusions such as water in honeycomb, and a high-pass filter may be included to highlight cracks in the structure of object 120. In an embodiment, cascaded multiple filters may be employed to produce final single images for viewing at real-time rates, or multiple filters may be individually applied to the same data to produce a set of images that may then be sub-sampled and displayed simultaneously in different regions of display 250, or different filters may be used to treat different images to produce a single composite image.

In an embodiment, process 500 is embodied in a computer program article 130, such as a compact disc read-only-memory (CD-ROM), a writeable CD, a rewriteable CD, or any other suitable storage medium, for example, that includes program instructions that is readable by a COTS processor.

Figure 3:
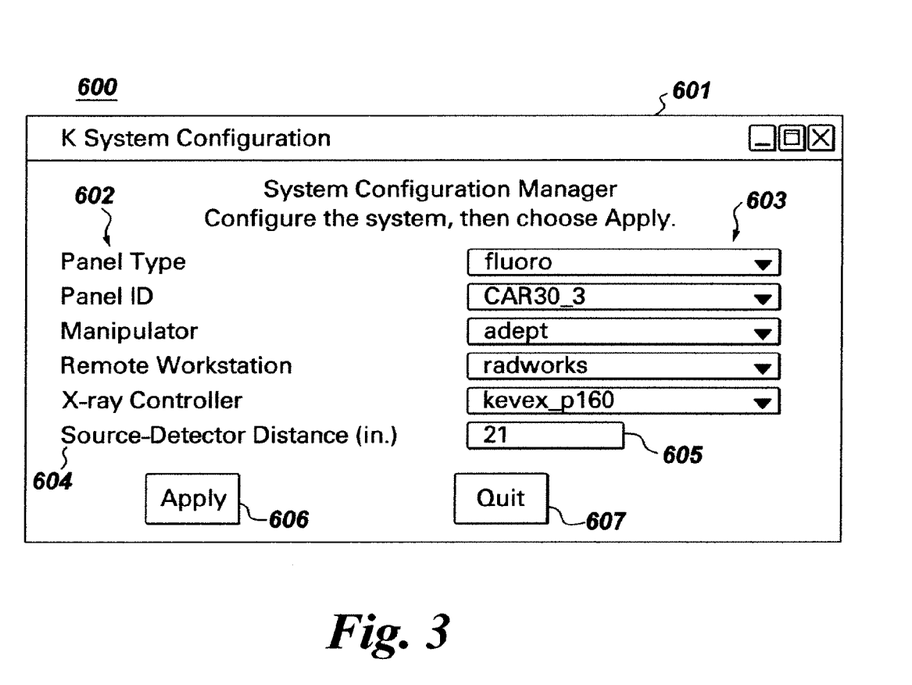
FIGS. 3-4 depict exemplary graphical user interfaces for carrying out an embodiment of the invention.
Figure 4:
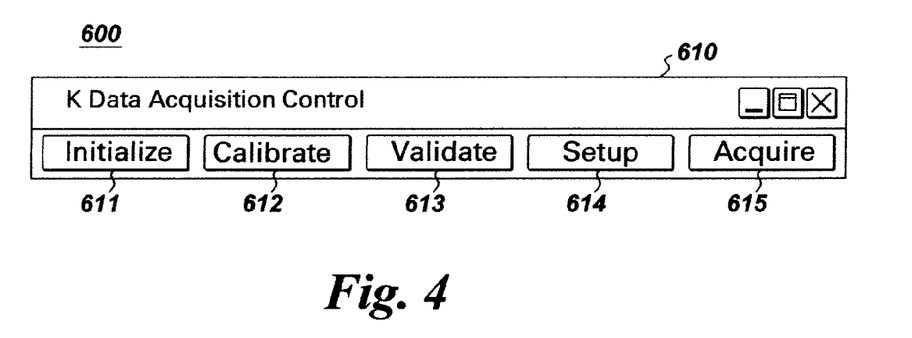

A user interfaces with inspection system 100 via a graphical user interface (GUI) 600, best seen by now referring to FIGS. 3-4, which depict screen shots of GUI 600 that are displayed on display device 250 and are responsive to input device 240. In general, GUI 600 provides the user with a set of interfaces that guide the user through various system selections, thereby enabling the user to acquire high quality digital images. GUI 600 is embedded in the application software in memory 230 and executed by processor 210.

Referring now to FIG. 3, GUI 600 is operable to perform a system configuration using a configuration software program 601, which prompts the user to select system hardware devices 602 to be controlled via drop-down menus 603. For example, and as depicted at 602, 603: the "Panel Type" (image detector 320) may be a "fluoro" (fluoroscopic) type panel with a "Panel ID" (identification) of "CAR30_3"; the "Manipulator" (330) may be an "adept" type manipulator; the "Remote Workstation" (controller 340) may be a "radworks" type workstation; and the "X-ray Controller" (x-ray source 310) may be a "kevex_p160" type x-ray source. The designations depicted at 603 are internal names for the software modules that control various required and optional components of the inspection system, such as detector 320, manipulator 330, image review station 340 and x-ray source 310. Other hardware devices 602 may be selected via drop-down menu 603, or no hardware device may be selected for optional components, in which case the user will be prompted to provide manual control inputs at the appropriate time. Configuration software program 601 also enables the user to input the "Source-Detector Distance (in.)" 604 in inches (in.) by entering a number such as "21" in input box 605. Upon completion of the configuration software program entries, the user selects either the "Apply" 606 or "Quit" 607 selection buttons. In response to a "Quit" selection, configuration software program 601 is terminated without a change being made in the system selections. In response to an "Apply" selection, configuration software program 601 instructs the application software to reconfigure itself, using manufacturer supplied configuration scripts that are stored in memory 230, to properly interface with the selected hardware. The configuration scripts may be stored in a lookup table in memory 230, which contains all of the hardware control parameters and drivers that are provided by the hardware manufacturer. If the user wants to use a particular hardware that is not in the lookup table, then an installation procedure may be followed to install the appropriate hardware control parameters and drivers and to create a new configuration script with its related drop-down menu entry.

Once inspection system 100 is configured, the user may begin using inspection system 100 for radiographic inspection, which involves the sequential activation of a multi-button taskbar (Sequencer) 610, best seen by now referring to FIG. 4, that includes, from left to right, "Initialize" 611, "Calibrate" 612, "Validate" 613, "Setup" 614, and "Acquire" 615 selection buttons. Sequencer 610 is configured to step the user, from left to right, through a logical set of pre-acquisition processes in order, thereby enabling ease of use setup and resulting in an inspection system that will operate in a predictable manner. The user is permitted to back up in the sequence to re-do previously performed steps, but cannot advance until the current step has been properly performed. In parallel to the display and operation of sequencer 610, a read-only system status display (not shown) reflects the current state of inspection system 100. The selection of a sequencer button launches the underlying software module in the application software for performing the particular task.

In response to a system initialization command by the user clicking on the "Initialize" button 611, the application software of inspection system 100 performs a power-on self-test of all of the connected hardware devices that have been selected using configuration software program 601. In response to a system calibration command by the user clicking on the "Calibrate" button 612, the application software prompts the user to either create new pixel offset correction maps and new pixel gain maps using known methods or to optionally use maps created during the prior calibration. New maps are stored at memory 230.

In response to a system validation command by the user clicking on the "Validate" button 613, the user has the option of running a validation algorithm within the application software to acquire sets of dark and flat field images and to scan a predefined composite test phantom to produce test images that are then used to analyze and measure several image quality and detector performance parameters. By successfully running a validation test and verifying that the operational parameters fall within a specified range, the operator can be confident that the system is configured properly to provide x-ray images with good image quality. Optionally, the user may bypass the system validation process.

Figure 5:
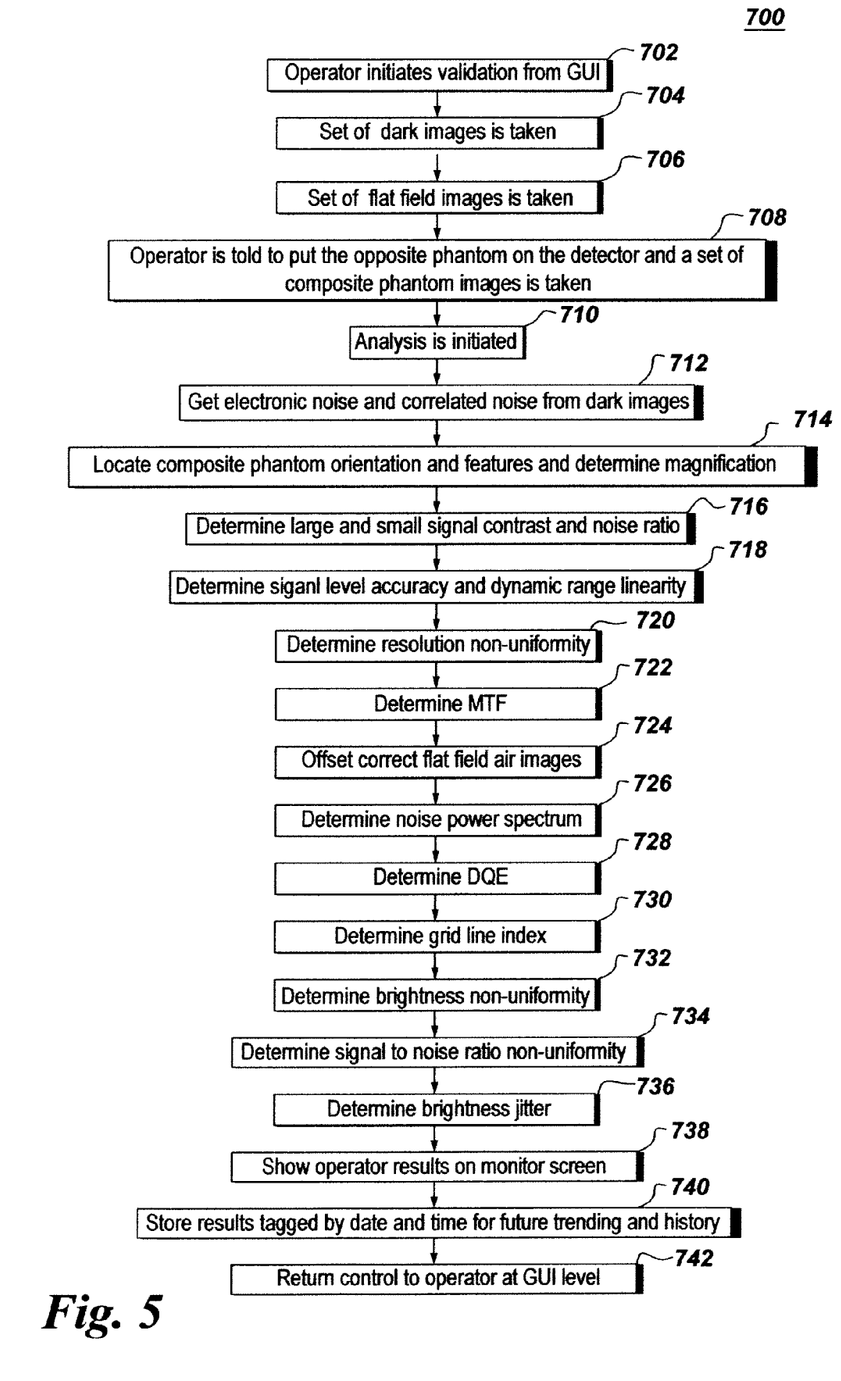
FIG. 5 depicts an exemplary process flow diagram in accordance with an embodiment of the invention.

Referring now to FIG. 5, an exemplary validation process 700 is depicted, which is initiated 702 by the user selecting the "Validate" button 613 at sequencer 610. At block 704, inspection and imaging systems 100, 300 take a set of dark images (no x-rays), which are stored at memory 230. At block 706, a set of flat field images (with x-rays on and with no object in the beam path) is taken. At block 708, the user is prompted to place the composite test phantom (depicted generally as object 120) within imaging device 305 and a set of composite phantom images are taken. At block 710, application software initiates analysis of the composite test phantom.

At block 712, electronic noise and correlated noise are determined from the pixel values of the set of dark images. Electronic noise, the noise of detector 320 with no external signal, is measured by reading several regions of interest within the dark images, and is the average of the mean pixel values of these individual regions. Correlated noise is the standard deviation of the mean pixel values taken from several regions of interest within the dark images. At block 714, the orientation and features of the composite phantom are located and the image magnification is determined.

At block 716, the large and small signal contrast and the contrast noise ratio are determined. The large signal contrast is determined using a through hole and a lead slug within the composite phantom image, acquiring the mean of the pixel values within each of these features, and calculating the difference of the means divided by the mean of the through hole. The small signal contrast is determined using an aluminum step wedge with through holes on each step within the composite phantom image, acquiring the mean of the pixel values on each step and on each hole on each step, and calculating the difference of the step and hole means per step divided by the mean of the through hole on the step. The contrast noise ratio (CNR) is determined using an aluminum step wedge with through holes on each step within the composite phantom image, acquiring the mean and standard deviation of the pixel values on each step and the mean of the pixels of each hole on each step, and calculating the difference of the step and hole means per step divided by the standard deviation on the step. All step contrast noise ratios are reported.

At block 718, the signal level accuracy and dynamic range linearity are determined. The signal level accuracy is a measure of the ability of the system to deliver the reference gray level to the output image, and is determined using copper step wedge within the composite phantom image and calculating the mean of pixel values (gray level) on each step. At the given exposure parameters, the measured levels should consistently achieve the target gray level. The accuracy is a summation measure using the normalized sum of squared differences of the actual and target gray levels. The dynamic range linearity is determined using a copper wedge within the composite phantom image, and calculating the mean of pixel values (gray level) on each step to measure the linearity of detector 320. The linearity is defined as the R-squares estimate from a linear regression fit with a straight line where the linearity is a measure of the mean absolute deviation in the log mean of the gray values.

At block 720, the Resolution Non-Uniformity (RNU) is determined by using several regions of interest within the various locations of mesh of the composite phantom image. The minimum and maximum of the mesh regions mean pixel values and the average of the mesh regions means are determined and calculated. The RNU is calculated from the difference of the maximum and minimum mesh region means divided by the average of the mesh region means.

At block 722, the Modulation Transfer Function (MTF) is determined. The MTF expresses the contrast of an object as a function of object detail. Tungsten coupon edges are used within the composite phantom image to determine MTF, which is a measure of the spatial frequency response in line pairs per millimeter. The MTF is a means for quantifying resolution and visually perceived sharpness. Low MTF values imply fuzzy images. High MTF values imply fine image detail. The MTF results are used in the determination of the Detective Quantum Efficiency (DQE) metric. At block 724, an offset correction is performed using flat field air images.

At block 726, the Noise Power Spectrum (NPS), which is a measure of the noise of detector 320 as a function of spatial density, is determined using the standard Fast Fourier Transform (FFT) method for the power spectrum. The set of offset corrected flat field air images is used to calculate the noise power spectrum at frequencies of interest in line pairs per millimeter. The noise power spectrum results are used in the determination of the Detective Quantum Efficiency (DQE) metric.

At block 728, the DQE is determined. The DQE is expressed as a function of object detail or spatial frequency, which combines noise and contrast performance as a measure of digital image quality and object detectability. At a particular frequency of line pairs per millimeter, the DQE is determined by multiplying an x-ray-dose correction factor times the square of the MTF at that frequency, divided by the NPS at that frequency.

At block 730, the grid line index is determined. The grid line index measurement compares the system performance against that performance that would be achieved using x-ray film. Several regions of interest of an offset corrected flat field air image are analyzed for the grid line spectrum by taking a two dimensional FFT of the pixel values and obtaining the pixel index at the estimated grid line frequency that would correspond to film. The maximum grid line index of the various regions of interest is reported.

At block 732, the brightness non-uniformity is determined by using an offset corrected flat field air image and by taking several overlapping regions of interest that cover most of the image. Over all of the individual regions of interest, the minimum and maximum of the regions mean pixel values and the average of the regions means are determined. The brightness non-uniformity is calculated from the difference of the maximum and minimum region means divided by the average of the region means.

At block 734, the Signal to Noise Ratio (SNR) non-uniformity is determined. The pixel means of several regions of interest in the set of offset corrected flat field air images are acquired, and a difference image from two of the offset corrected flat field air images is created. The pixel standard deviations of matching regions of interest in the difference image are calculated, and then normalized by dividing by the square root of two. The SNR is the ratio of calculated signal intensity to the random intensity (noise) variations, and is calculated for each region of interest by dividing the mean standard deviation by the normalized standard deviation. A determination is made of the minimum, maximum and mean of the signal to noise ratios of the regions of interest, and the SNR non-uniformity calculated by taking the difference of the maximum and minimum SNRs divided by the mean of the SNRs.

At block 736, the brightness jitter is determined. The brightness jitter measures the temporal brightness uniformity in grayscale using a sequence of offset corrected flat field air images. Mean gray levels are measured for each image inside a single region of interest of given size and location. The mean gray level is calculated for each image's region of interest. For all images, the standard deviation of the means and the average of the means are calculated. The brightness jitter is calculated as the standard deviation divided by the average.

At block 738, the results are displayed on display device 250 for operator viewing. At block 740, the results are tagged by date and time for future trending and history. At block 742, application software returns control to the operator at GUI 600.

Regarding the parameters of process 700: the dark images are used to report on the electronic noise and correlated noise metrics, and to offset correct the flat field air images; the offset corrected flat field air images are used to report on the metrics of brightness non-uniformity and brightness jitter, signal to noise non-uniformity, grid line index and the noise spectrum; the offset corrected composite phantom images are used to report on the metrics of the spatial MTF, resolution non-uniformity, small signal contrast, large signal contrast, signal level accuracy, dynamic range linearity and contrast noise ratio; and, combining the MTF metric with the noise power spectrum produces a DQE measurement.

Referring now back to FIG. 4, after "Validate" and in response to a system setup command by the user clicking on the "Setup" button 614 at sequencer 610, an operator that has been granted a high level of capability is guided through several setup windows 800, 825, 850, 875, best seen by now referring to FIGS. 6-9, that allow the operator to make all of the parameter selections available for the acquisition based upon the components in inspection system 100. These parameter settings can be saved at memory 230 and recalled for future use as a named technique. Operators that have been granted a lesser level of capability can choose named techniques set up by the high level operators, but cannot change most parameters. The parameters may include but are not limited to x-ray 310, display 250, manipulator 330, and detector 320 settings, real-time initialization values, and initial image processing parameters. Also, the choice may be made to use gain and offset tables from the calibration process or to acquire new gain and offset tables just prior to the image acquisition. By acquiring new tables just prior to acquisition, the effects of any non-uniformities that may have arisen during prior imaging can be normalized out of the acquired images. The choice may also be made to not apply gain and offset correction; and a choice can be made not to correct for non-functional pixels so that raw data can be acquired.

Once the operator has passed the "Validate" stage, the operator can toggle between the "Setup" button 614 and the "Acquire" button 615 on the sequencer 610, thereby enabling the operator to re-adjust parameters and repeat an acquisition or set up for a new acquisition. This toggling feature is especially helpful when operating inspection system 100 in real-time mode where transient non-uniformities occur while still acquiring images.

Referring to FIGS. 6-9 generally, know GUI navigation tools such as "tabs", "input boxes", "drop down menus", yes/no "check boxes", selection "check boxes", and "activation buttons", are used and discussed further below. While in setup (activation of "Setup" button 614), four "tabs", referred to as setup dialog tabs with associated setup dialog screens, are displayed at the top of the screen at display 250: "General" 802; "Acquisition" 827; "X-ray" 852; and "Image Control" 877, which will be discussed separately below. Clicking on one of these tabs brings up the setup dialog screen as depicted in FIGS. 6-9. At the bottom of each screen is a set of activation buttons 801 labeled: "Accept & Continue"; "Archive & Continue"; and "Cancel". The "Accept & Continue" button checks all of the setup dialog screen fields for correctness, outputs the information to a file used by the software in the "Acquire" step, and proceeds to the "Acquire" button. Any operator changes are not recorded and saved to the database. The "Archive & Continue" button performs all of the actions and steps of the "Accept & Continue" button and in addition saves all of the setup parameters to a database for future reference and use, which is recorded under a technique name discussed below. The "Cancel" button returns control to the operator at sequencer 610. As used herein, quotations refer to screen elements within the setup dialog screens. While FIGS. 6-9 depict various input and/or selection boxes, it will be appreciated that these are exemplary only and that other input and/or selection boxes may be used in their place. For each setup window of FIGS. 6-9, the application software reviews an entry at an input box for validity. If a valid entry is made, the entry is accepted, if an invalid entry is made, the operator is notified and a new entry is requested.

Figure 6:
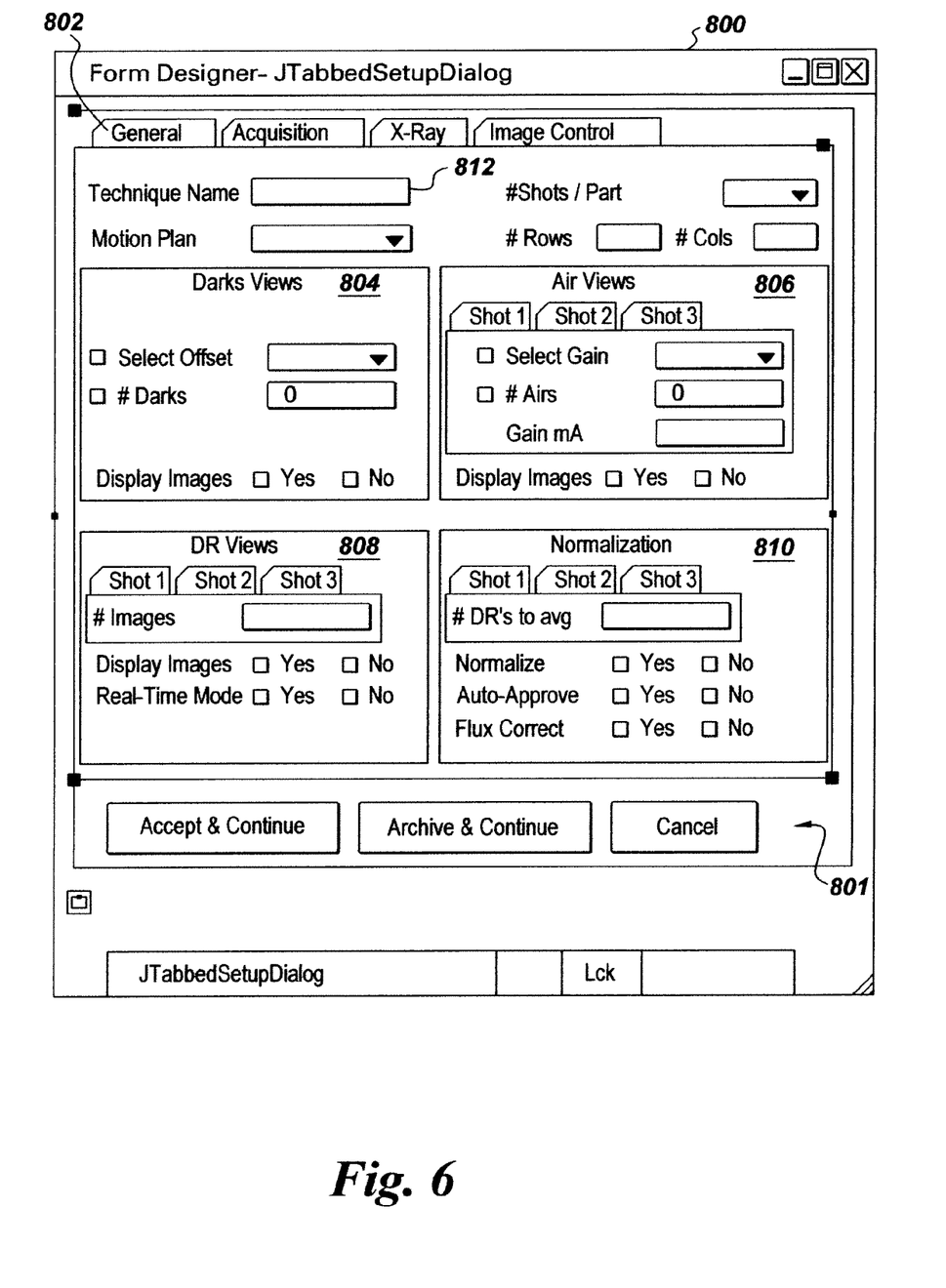
FIGS. 6-9 depict exemplary graphical user interfaces for carrying out an embodiment of the invention.

Referring now to FIG. 6, setup window 800 depicts setup parameters for the "General" tab 802, where various parameters associated with "Dark Views" 804, "Air Views" 806, "DR (digital radiographic) Views" 808, and "Normalization" 810, may be input and/or selected for "Shots 1-3". "Dark Views" refers to images taken with no x-ray exposure. "Air-Views" refers to images taken with x-ray exposure, but with no object in the x-ray beam. "DR Views" refers to images taken with x-ray exposure with an object in the x-ray beam. "Normalization" refers to the process of offset and gain correction. "Shots 1-3" refers to an embodiment where up to 3 orientations of an object may be specified. In addition, the operator can choose to name the setup with a "Technique Name" 812. Alternatively, upon entering "General" tab 802, the operator can enter a "Technique Name" and accept the selections associated therewith.

Figure 7:
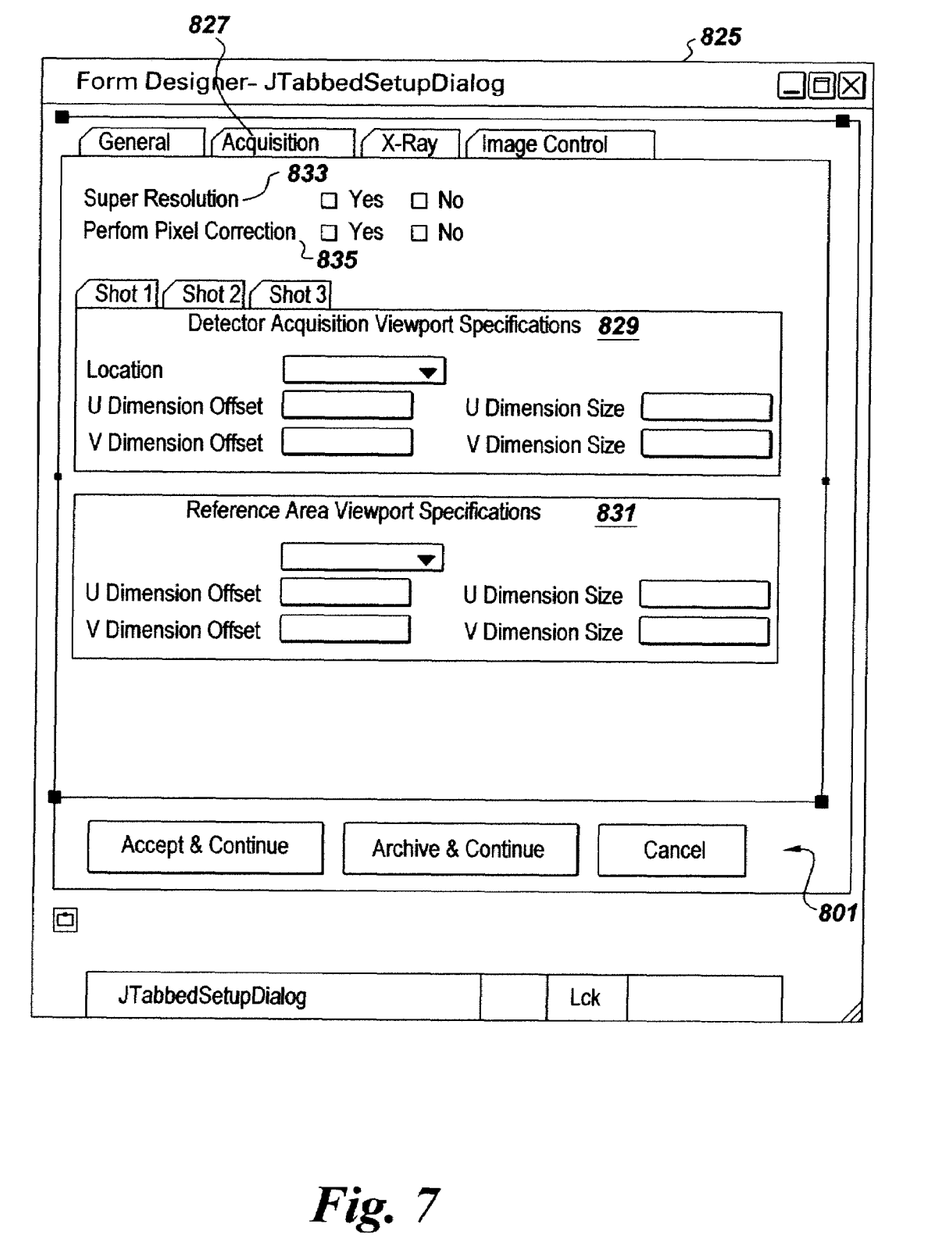

Referring now to FIG. 7, setup window 825 depicts setup parameters for the "Acquisition" tab 827, where various parameters associated with "Detector Acquisition Viewport Specifications" 829 and "Reference Area Viewport Specifications" 831 may be input and/or selected for "Shots 1-3". "Detector Acquisition Viewport Specifications" refers to picking a region of interest for storage within an image. "Reference Area Viewport Specifications" refers to picking an area within an image for storing an average pixel value of that area in the image header. Also at setup window 825, the operator may select whether to include or exclude "Super Resolution" 833 and "Perform Pixel Correction" 835 "Super Resolution" refers to an embodiment of the system that includes achieving a higher resolution image by spatially oversampling the detector. "Perform Pixel Correction" refers to correcting for non-functional pixels.

Figure 8:
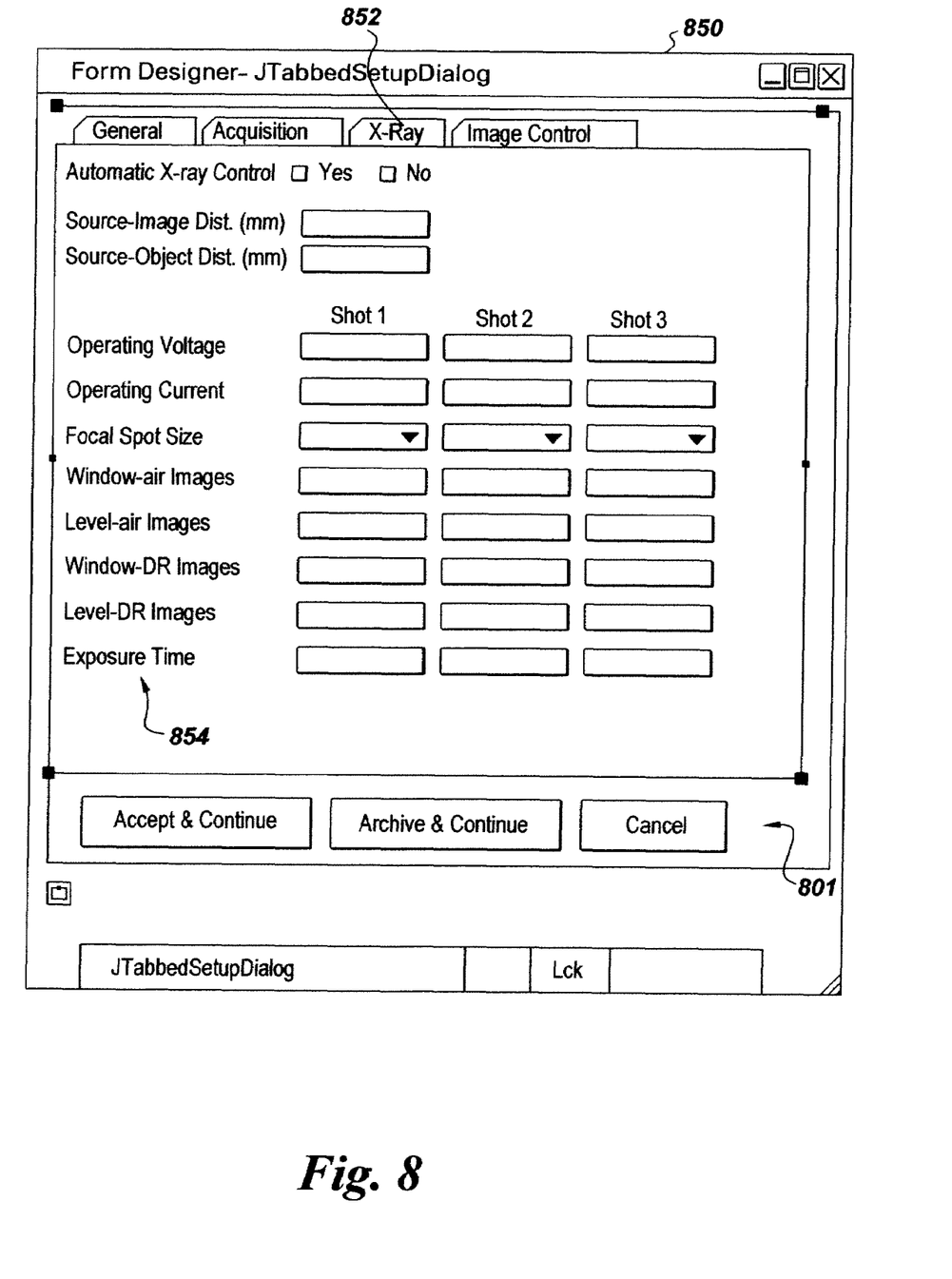

Referring now to FIG. 8, setup window 850 depicts setup parameters for the "X-ray" tab 852, where various parameters associated with the x-ray source 310 may be input and/or selected for "Shots 1-3". For example, the operator may select at 854 whether to have "Automatic X-ray Control" for x-ray source 310, may input the "Source-Image Distance (mm, millimeters)", may input the "Source-Object Distance (mm)", may input the x-ray "Operating Voltage" for x-ray source 310, may input the "Operating Current" for x-ray source 310, may select the "Focal Spot Size" for x-ray source 310, may input the "Window (image contrast)—air images", may input the "Level (image brightness)—air images", may input the "Window (image contrast)—DR images", may input the "Level (image brightness)—DR images", and may input the "Exposure Time" in milliseconds (msec) for x-ray source 310.

Figure 9:
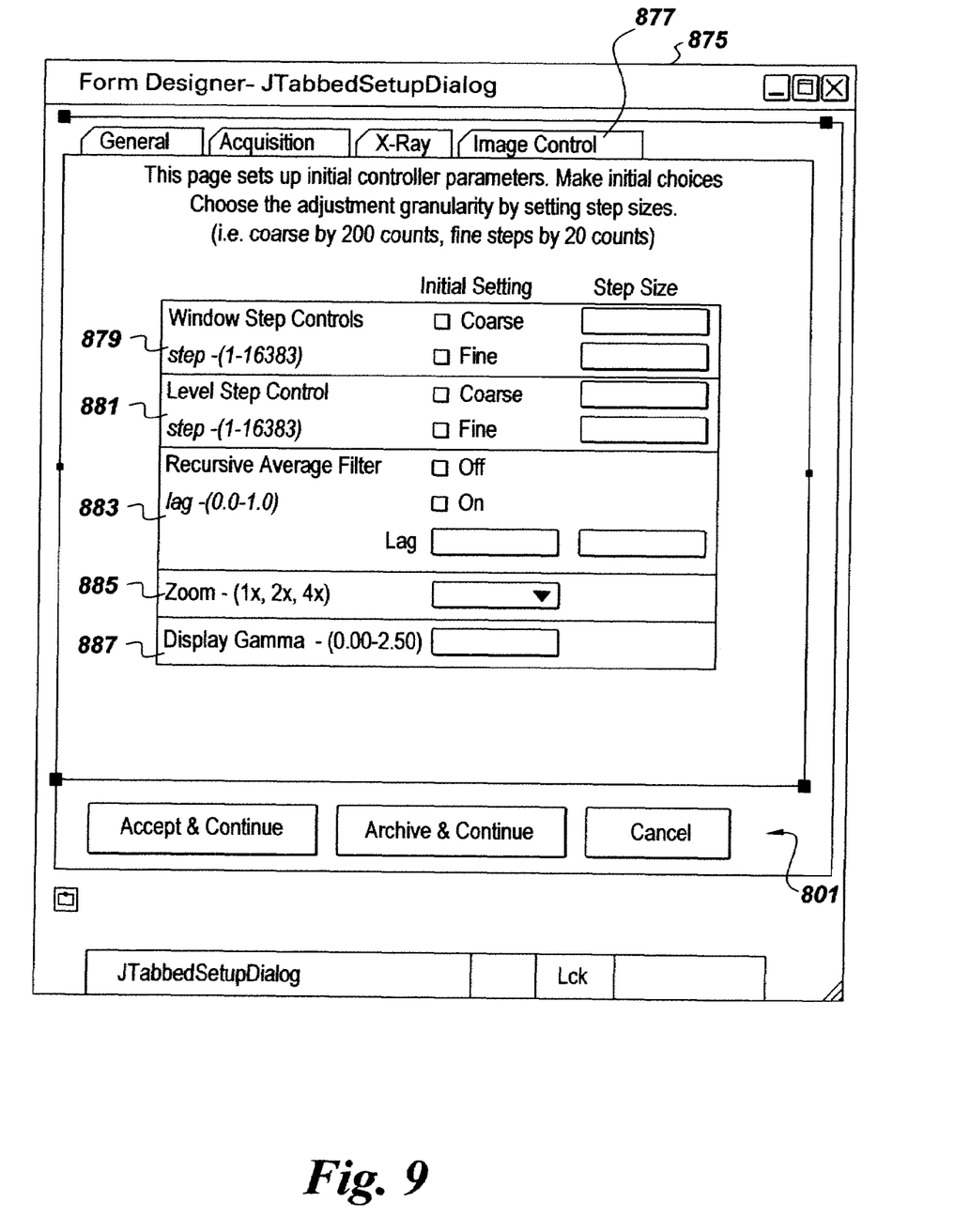

Referring now to FIG. 9, setup window 875 depicts setup parameters for the "Image Control" tab 877, where various parameters associated with "Window (image contrast) Step Controls" 879, "Level (image brightness) Step Controls" 881, "Recursive Average Filtering" 883, image "Zoom" 885, and "Display Gamma" 887, may be input and/or selected. The gamma input value associated with the displayed image enables the operator to control the pixel intensity as a function of detected voltage, where intensity varies as a function of voltage-raised-to-the-power-of-gamma.

Completion of the setup process, that is, completion of the entries at setup windows 800, 825, 850, 875, returns control to the operator at sequencer 610. Referring now back to FIG. 4, after "Setup" and in response to a system acquisition command by the operator clicking on the "Acquisition" button 615 at sequencer 610, the operator is prompted whether to operate inspection system 100 in real-time mode or static DR (digital radiographic) mode, and in response thereto inspection system 100 enters the selected mode.

Figure 10:
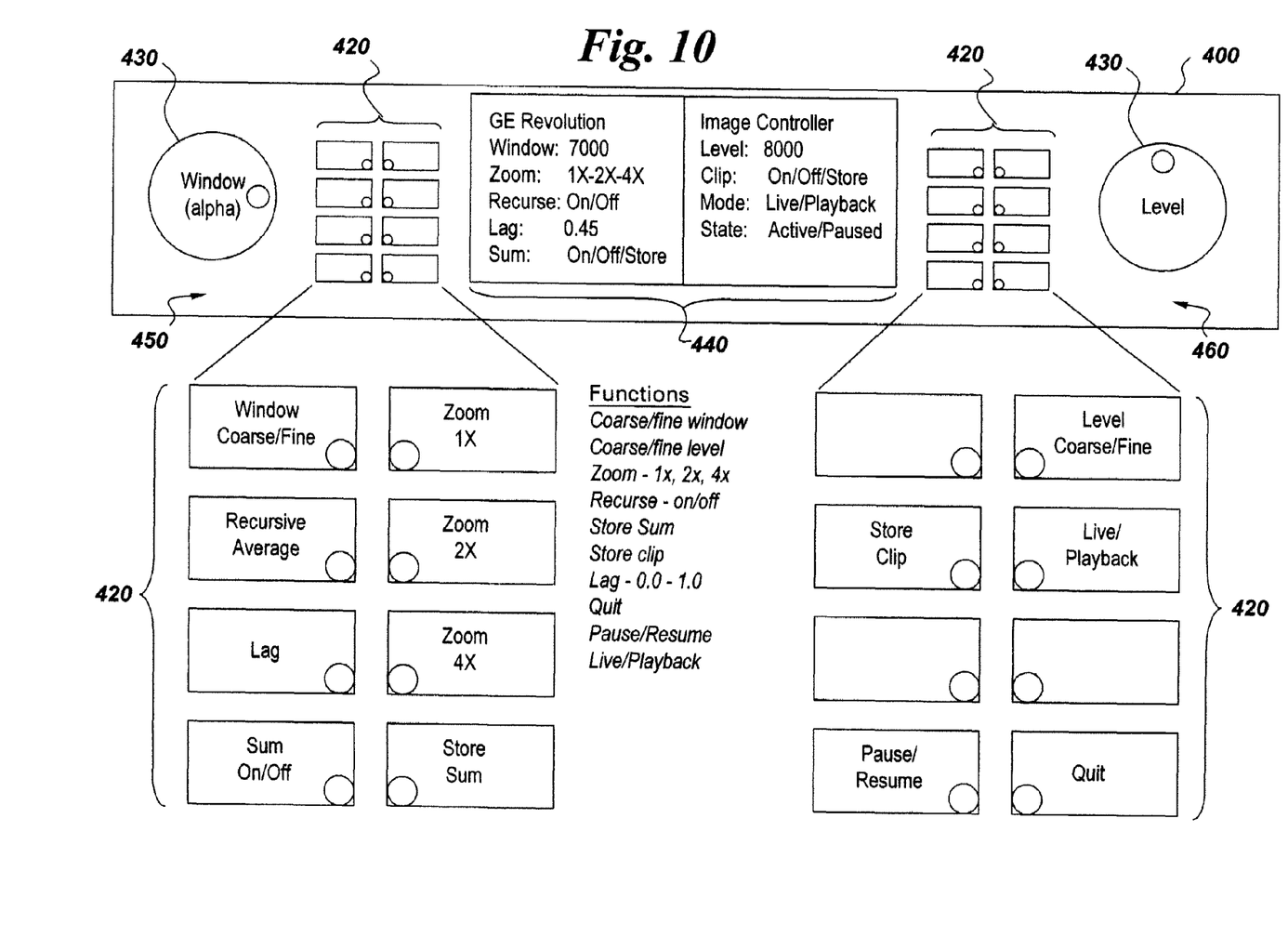
FIG. 10 depicts an exemplary real-time image controller in accordance with an embodiment of the invention.

In response to inspection system 100 being operated in real-time mode, the hardware controls available to interactively manipulate the real-time imagery are enabled via real-time image controller (RTIC) 400, which is best seen by referring to FIG. 10. As discussed above, RTIC 400 includes a set of image control buttons 420, a set of image control dials 430, a display 440, and an embedded application programming interface that maps the functions of control buttons and dials 420, 430 to the application software at computer 200. Communication between RTIC 400 and computer 200 is via communication bus 410, which in an embodiment is a serial port. In an embodiment, RTIC 400 is a commercial off the shelf (COTS) controller box that is available with an associated application programming interface (API The application software at memory 230 implements the functions selected by the operator by sending appropriate commands to the appropriate software modules of the application software. The control button and control dial functions of RTIC 400 are defined by the application software and are depicted in FIG. 10. Not all functions of RTIC 400 may be available at all times, and since a COTS controller box may be employed, not all buttons may have an associated function. Accordingly, FIG. 10 depicts only one exemplary embodiment of RTIC 400, and it is contemplated that other real-time image controllers may be employed in accordance with the teachings of this invention.

Referring now to FIG. 10, in an embodiment of RTIC 400, the left set 450 of control buttons 420 and control dial 430 includes "Window—Coarse/Fine", "Recursive Average", "Lag", "Sum—On/Off", "Zoom", and "Store Sum" controls, and the right set 460 of control buttons 420 and control dial 430 includes "Store Clip", "Pause/Resume", "Level—Coarse/Fine", "Live/Playback", and "Quit". Display 440 shows the operator the current state of the controller functions.

Regarding the left set 450 of dial 430 and buttons 420, dial 430 either adjusts the value of "Window" or "Lag" up or down depending on which function is active and which direction the dial is turned, with a clockwise rotation increasing the value. When the "Window—Coarse/Fine" button is turned on, the left 450 dial 430 controls the display contrast in fine step sizes (defined at setup window 875 and discussed above), and when turned off, the left 450 dial 430 controls the display contrast in coarse step sizes. When the "Recursive Average" button is turned on, the recursive average image processing algorithm is on and uses the current lag parameter, and when turned off, the recursive average image processing algorithm is off. In an embodiment, the recursive average algorithm employs an exponential weighting function as discussed above. The "Lag" button is only available when the "Recursive Average" button is on. When the "Lag" button is turned on, the left dial 430 increases or decreases the lag parameter based on the lag step size defined at setup window 875, and when turned off, the left dial 430 controls the "Window" function. When the "Sum—On/Off" button is turned on, up to 1,000 consecutive frames are summed together (an image processing technique), and when turned off, the ability to sum frames is turned off. The frame summation function and the recursive averaging function are mutually exclusive. The "Zoom" buttons provide 1×, 2× and 4× zooming of the displayed image. When one of the "Zoom" buttons is on, the image is zoomed and displayed by the selected amount. The three "Zoom" buttons are mutually exclusive. The "Store Sum" button permits the operator to store the single summed image resulting from activation of the "Sum—On/Off" button. In an embodiment, the operator would store the summed image before live acquisition or playback is resumed, and would either store the summed image in a standard image processing format either locally at memory 230 or send it to display 250.

Regarding the right set 460 of dial 430 and buttons 420, dial 430 adjusts the value of "Level" up or down depending on which direction the dial 430 is turned, with a clockwise rotation increasing the value. When the "Store Clip" button is on, up to ten seconds (configurable) of consecutive frames (a movie) is either stored in a standard image processing format either locally at memory 230 or sent to display 250. The amount of host computer memory limits the length of this clip. In an alternative embodiment, processed frames are stored on a high speed disk array in real time. In this configuration, clip duration can exceed 10 seconds and is limited by the amount of disk space available on the disk array. Stored images may be saved via a video signal output for recordation on a video cassette recorder (VCR) tape or a DVD recorder generally depicted at 140. Recording directly from the provided video signal does not limit the length of imagery that can be stored to these media. When the "Pause/Resume" button is on, the current mode is in a paused state. To resume the current mode (playback or live acquisition), the button is turned off. A pause function may occur at other times during acquisition without operator interaction. For example, if "Sum—On/Off" was turned on then off, RTIC 400 will go into a paused state, which allows the operator time to store the image if so desired. When the "Level—Coarse/Fine" button is on, right 460 dial 430 controls the display brightness in fine step sizes (defined at setup window 875 and discussed above), and when off, right dial 430 controls the display brightness in coarse step sizes. When the "Live/Playback" button is on, RTIC 400 is in playback mode looping through up to the last ten seconds of acquired data. The "Quit" button allows the operator to quit the real-time mode and return to the main GUI 600.

It is contemplated that other real-time dynamic functions may also be incorporated into RTIC 400, such as image panning, x-ray energy control, and gamma control. The gamma parameter characterizes the non-linear relationship between an image pixel value and computer monitor hardware display intensity and allows for the effect of perceived brightness to be corrected. These additional functions may be controlled by the untitled buttons 420 on the right side 460 of RTIC 400.

In response to inspection system 100 being operated in static DR (digital radiographic) mode, image acquisition is automatically performed from the parameters as set in the acquisition technique setup ("Setup" button 614) for those system hardware devices being controlled by inspection system 100. If a component is not being controlled by inspection system 100, and embedded application software, then the operator is directed to provide a manual control input for that particular device. For example, if x-ray source 310 is not being controlled by inspection system 100, then the operator will be instructed to set the x-ray voltage and current or turn the x-rays on or off at the appropriate time. If manipulator 330 is not controlled by the system, the operator will be instructed when to place object 120 in position for inspection at the proper time. When operating in static DR mode, inspection system 100 is capable of storing full frame or region-of-interest corrected images, which may be averaged together.

In both static DR and real-time mode, the acquisition technique setup allows for either use of gain and offset tables from the calibration step, or for acquisition of new gain and offset tables at image acquisition time. The advantage of creating new gain and offset tables just prior to acquisition reduces the perception of transient non-uniformities (e.g., hysteresis, variations in x-ray profile) in the acquired images. In real-time mode, if these effects begin to creep in, the operator merely needs to quit the real-time acquisition and begin again, re-acquiring a new set of gain and offset tables to apply as subsequent real-time acquisition transpires. In static DR mode, stored images from RTIC 400 go to the review station, while captured images first get shown to the user for approval prior to being sent to the review station. Images are sent to the review station in standard image processing format. As discussed above, the software architecture of inspection system 100 is command driven. Each type of component in the system has a known set of generic commands that it can execute. All x-ray controllers that can be configured to be part of the system, for example, may be configured to handle the same set of generic commands, where the software translates the generic commands to hardware specific commands for a particular x-ray controller. Each task in the system is accomplished through a given a set of instructions performed across the various process components. Task steps are synchronized among the various multi-threaded processes taking advantage of parallel execution where possible. In addition, while inspection system 100 is depicted in FIG. 1 having a computer 200, it will be appreciated that inspection system 100 may span multiple computers and operating systems through the use of a carefully constructed communication interface. The architecture of inspection system 100 is configured in such a way that it is relatively easy to add new components such as a new x-ray tube controller through the setup configuration software program described above, with all operational processes reporting errors to a single point in the control process. The application software in inspection system 100 directs all processes to gracefully and safely shut down in the case of a fatal error in one of the processes. For example, if manipulator 330 encounters a fatal error, the x-ray process is notified to shut down and x-rays are turned off before the x-ray process exits. At any time the operator may also choose to exit the system through the sequencer task bar, sequencer 610. A system exit will direct all processes to gracefully and safely shut down all system components and interfaces.

Some embodiments of the invention have some of the following advantages: non-destructive real-time radiographic imaging at real-time rates equivalent to 30 million pixels per second; ease of hardware interchange (through the setup configuration software program) without need to revalidate entire system; controlled setup dependent on skill level of the operator; ease of use configuration software program; ease of use sequencer taskbar; detection of incorrect parameters in setup tables; use of commercial off the shelf processor for real-time image processing; use of commercial off the shelf programmable real-time image controller box; real-time image manipulation; real-time digital enhancement of x-ray images; system feedback to operator through graphical user interface; embedded detector validation diagnostics; capability to archive real-time inspection procedures to videotape; capability to archive selected inspection data to compact disc or DVD in real-time; capability to create new gain and offset tables just prior to acquisition, or to acquire the same from a calibration set in memory; capability to reduce visual effects of hysteresis in the detector panel; and capability to enhance image quality in real-time.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A radiographic inspection system, comprising:
   a computer adapted to be in signal communication with an imaging system, the imaging system adapted to acquire and output radiographic image data of a scanned object; and
   a real-time image controller in signal communication with the computer;
   the computer comprising:
   a processor to execute operations according to a set of instructions provided by installed application software;
   at least one memory to store the application software and to store the image data; and
   an input device and a display device operable as a graphical user interface to configure and operate the inspection system;
   the real-time image controller comprising:
   at least one of a set of image control buttons and a set of image control dials; and
   an application programming interface to map the functions of the control buttons and dials to the application software.

2. The system of claim 1, wherein the application software and graphical user interface are operable to perform a system configuration using a configuration software program, and to perform at least one of system initialization, system calibration, system validation, system setup, and data acquisition.

3. The system of claim 2, wherein:
   the configuration software program prompts the user to select available system hardware devices to be controlled, the hardware devices including at least one of a radiographic source, a manipulator, and an image detector, and to select at least one of the mode of operation and the source to image distance; and
   in response to a user command, the configuration software program instructs the application software to reconfigure itself, using configuration scripts, to properly interface with the selected hardware.

4. The system of claim 2, wherein:
   in response to a system initialization command, the system performs a power-on self test of at least one of the connected hardware devices;
   in response to a system calibration command, the user may selectively create pixel offset correction maps and pixel gain maps, or may opt to use maps created during the prior calibration;
   in response to a system validation command, the user may selectively scan a test phantom to produce a test image that the application software analyzes to measure and report image quality and detector performance parameters, or may opt to bypass a system validation process;
   in response to a system setup command, the user is guided though a series of system setup windows that permit the user to select acquisition parameters based on the available system hardware, the parameters available for selection being dependent on the skill level of the user, the parameters including at least one of x-ray, display, manipulator, and detector settings, real-time initialization values, initial image processing parameters, and the selection of gain and offset tables from the calibration process or from tables newly acquired prior to image acquisition; and
   in response to a data acquisition command, the user is prompted to select a real-time mode or a static mode, and in response thereto the system enters the selected mode.

5. The system of claim 4, wherein:
in response to the selection of the real-time mode, the real-time image controller is enabled, which instructs the application software to make appropriate image processing adjustments according to the settings of the image control buttons and dials, the buttons and dials controlling at least one of image contrast, brightness, zoom, and playback.

6. The system of claim 5, wherein the image control buttons and dials further control at least one of coarse and fine adjustment with user definable step sizes, recursive averaging with user selectable lag rate, frame summation, single full frame image storing, and multiple full frame image storing.

7. The system of claim 6, wherein the display device displays the radiographic image in real-time at a frame rate of equal to or greater than 30 million pixels per second.

8. The system of claim 4, wherein:
in response to the selection of the static mode, the system automatically acquires image data according to the parameters established at system setup for controlled system hardware devices, and in the event that a system hardware device is not controlled by the application software, the user is prompted to provide a manual control input for that device.

9. The system of claim 8, wherein:
in response to the system operating in static mode, the user may store at least one of a set of full frame images, and a set of region-of interest images, where each set of images may be averaged together.

10. The system of claim 2, wherein in response to a system validation command, the application software includes instructions for:
taking a set of dark images;
taking a set of flat field air images;
taking a set of object images;
getting electronic noise and correlated noise from the dark images;
determining a large and a small signal contrast and a contrast noise ratio;
determining a signal level accuracy and dynamic range linearity;
determining a resolution non-uniformity;
determining a modulation transfer function;
offset correcting the flat field air images;
determining a noise power spectrum;
determining a detective quantum efficiency;
determining a grid line index;
determining a brightness non-uniformity;
determining a signal to noise ratio non-uniformity;
determining brightness jitter;
displaying resulting images at a display; and
storing the resulting images tagged by at least one of a date and a time for future trending and history.

11. The system of claim 1, wherein the processor is programmed for:
performing in integer format a pixel offset correction on the radiographic image using saturation arithmetic to produce an image in integer format having negative value pixels clipped to a value of zero;
converting the resulting pixels to floating point format and multiplying the converted pixels by a gain factor;
converting the resulting pixels to integer format and clamping the converted pixel values to a maximum value using saturation arithmetic;
performing in integer format non-functional pixel correction and clamping the resulting pixel values to a maximum value using saturation arithmetic;
mapping in integer format the resulting pixel value to a palette index to establish an output pixel intensity having one of many intensity levels;
filtering the mapped radiographic image though a high-pass filter to enhance feature recognition within the thickness range of the scanned object; and
displaying the filtered radiographic image in real-time at a frame rate of equal to or greater than 30 million pixels per second.

12. The system of claim 11, wherein:
the performing a pixel offset correction comprises performing a dark image pixel subtraction from the radiographic image;
the integer format and the radiographic image are in 16-bit integer format;
the floating point format and the gain factor are in 32-bit floating point format;
the clamped pixel values are clamped to a 16 bit range and not allowed to wrap;
the palette index is in 8-bit integer format; and
the many intensity levels comprises at least 256 shades of gray.

13. The system of claim 12, wherein the processor is further programmed for:
performing in floating point format weighted averaging on the gain-multiplied pixels prior to converting the pixels to integer format and performing the non-functional pixel correction;
wherein the mapping the resulting pixel value to a palette index comprises mapping via a lookup table; and
wherein the gain factor is acquired from a normalization table.

14. The system of claim 12, wherein the processor is further programmed for:
adding the offset corrected pixels to an accumulation of zero or more offset corrected pixels to provide an accumulation of offset corrected pixels;
converting the resulting pixels to floating point format and multiplying the converted pixels by a gain factor;
dividing or multiplying by a reciprocal value the resulting pixels by the number of accumulated images;
converting the resulting pixels to integer format and clamping the converted pixel values to a maximum value using saturation arithmetic;
performing in integer format non-functional pixel correction and clamping the resulting pixel values to a maximum value using saturation arithmetic;
mapping in integer format the resulting pixel value to a palette index to establish an output pixel intensity having one of many intensity levels;
filtering the mapped radiographic image though a high-pass filter to enhance feature recognition within the thickness range of the scanned object; and
displaying the filtered radiographic image in real-time at a frame rate of equal to or greater than 30 million pixels per second.

15. The system of claim 14, wherein:
the performing a pixel offset correction comprises performing a dark image pixel subtraction from the radiographic image;
the integer format, the offset image, and the radiographic image are in 16-bit integer format;
the accumulation of offset corrected pixels is in 32-bit integer format;
the floating point format and the gain factor are in 32-bit floating point format;
the clamped pixel values are clamped to a 16 bit range and not allowed to wrap;
the palette index is in 8-bit integer format; and
the many intensity levels comprises at least 256 shades of gray.

* * * * *

UNITED STATES PATENT AND TRADEMARK OFFICE
CERTIFICATE OF CORRECTION

PATENT NO. : 7,522,756 B2  Page 1 of 1
APPLICATION NO. : 11/684176
DATED : April 21, 2009
INVENTOR(S) : Bueno et al.

It is certified that error appears in the above-identified patent and that said Letters Patent is hereby corrected as shown below:

In Column 14, Line 55, in Claim 4, delete "though" and insert -- through --, therefor.

In Column 16, Line 1, in Claim 11, delete "though" and insert -- through --, therefor.

In Column 16, Line 45, in Claim 14, delete "though" and insert -- through --, therefor.

Signed and Sealed this

Fourth Day of August, 2009

JOHN DOLL
*Acting Director of the United States Patent and Trademark Office*